United States Patent [19]

Dew et al.

[11] Patent Number: 5,140,984

[45] Date of Patent: * Aug. 25, 1992

[54] LASER HEALING METHOD AND APPARATUS

[75] Inventors: Douglas K. Dew, Maitland; Long S. Hsu, Orlando; Steven J. Halpern, Winter Park, all of Fla.

[73] Assignee: Proclosure, Inc., Winter Park, Fla.

[*] Notice: The portion of the term of this patent subsequent to Aug. 8, 2006 has been disclaimed.

[21] Appl. No.: 639,025

[22] Filed: Jan. 9, 1991

Related U.S. Application Data

[60] Continuation of Ser. No. 380,622, Jul. 14, 1989, Pat. No. 5,002,051, which is a division of Ser. No. 62,861, Jun. 16, 1987, Pat. No. 4,854,320, which is a continuation-in-part of Ser. No. 539,527, Oct. 6, 1983, Pat. No. 4,672,969.

[51] Int. Cl.⁵ ................................ A61N 5/06
[52] U.S. Cl. .................... 128/395; 128/397; 606/2; 606/11
[58] Field of Search ............ 129/395, 397, 398; 606/2, 3, 10, 11, 12, 37, 40, 49

[56] References Cited

U.S. PATENT DOCUMENTS

| | | | |
|---|---|---|---|
| 3,467,098 | 9/1969 | Ayres | 128/303.1 |
| 3,750,670 | 8/1973 | Palanos et al. | 128/303.1 |
| 3,769,963 | 11/1973 | Goldman et al. | 128/303.1 |
| 3,794,040 | 2/1974 | Baldmuth | 128/303.1 |
| 4,122,853 | 10/1978 | Smith | 128/303.1 |
| 4,209,018 | 6/1980 | Meinke et al. | 606/40 |
| 4,266,549 | 5/1981 | Kimura | 128/303.1 |
| 4,498,475 | 2/1985 | Schneiderman | 606/37 |
| 4,539,987 | 9/1985 | Nath et al. | 606/3 |
| 4,564,012 | 1/1986 | Shimada et al. | 128/395 |
| 4,672,969 | 6/1987 | Dew | 128/397 |
| 4,727,874 | 3/1988 | Bowers et al. | 606/40 |
| 4,827,927 | 5/1989 | Newton | 606/40 |
| 4,854,320 | 8/1989 | Dew et al. | 128/397 |
| 5,002,051 | 3/1991 | Dew et al. | 128/395 |

Primary Examiner—Theatrice Brown
Assistant Examiner—Jessica J. Harrison
Attorney, Agent, or Firm—Steven C. Stewart

[57] ABSTRACT

The method and apparatus of the invention use a beam of laser emitted optical energy to effect wound closure and reconstruction of biological tissue. In response to input as to tissue type and thickness, a computer determines the output power, exposure time and spot diameter of the emitted beam to control the application of optical energy to produce thermal heating of biological tissue to a degree suitable for denaturing the tissue proteins such that the collagenous elements of the tissue form a "biological glue" to seal immediately and/or to reconstruct the tissue being heated. In a given embodiment, the computer directly controls output power of the laser by regulating the laser's input current, and limits exposure time by deactivating a shutter mechansim when the determined time is reached. Beam diameter is manually set in response to a displayed value for a sliding scale that controls the working distance between the end of a fiber optic beam guide and the tissue site.

2 Claims, 3 Drawing Sheets

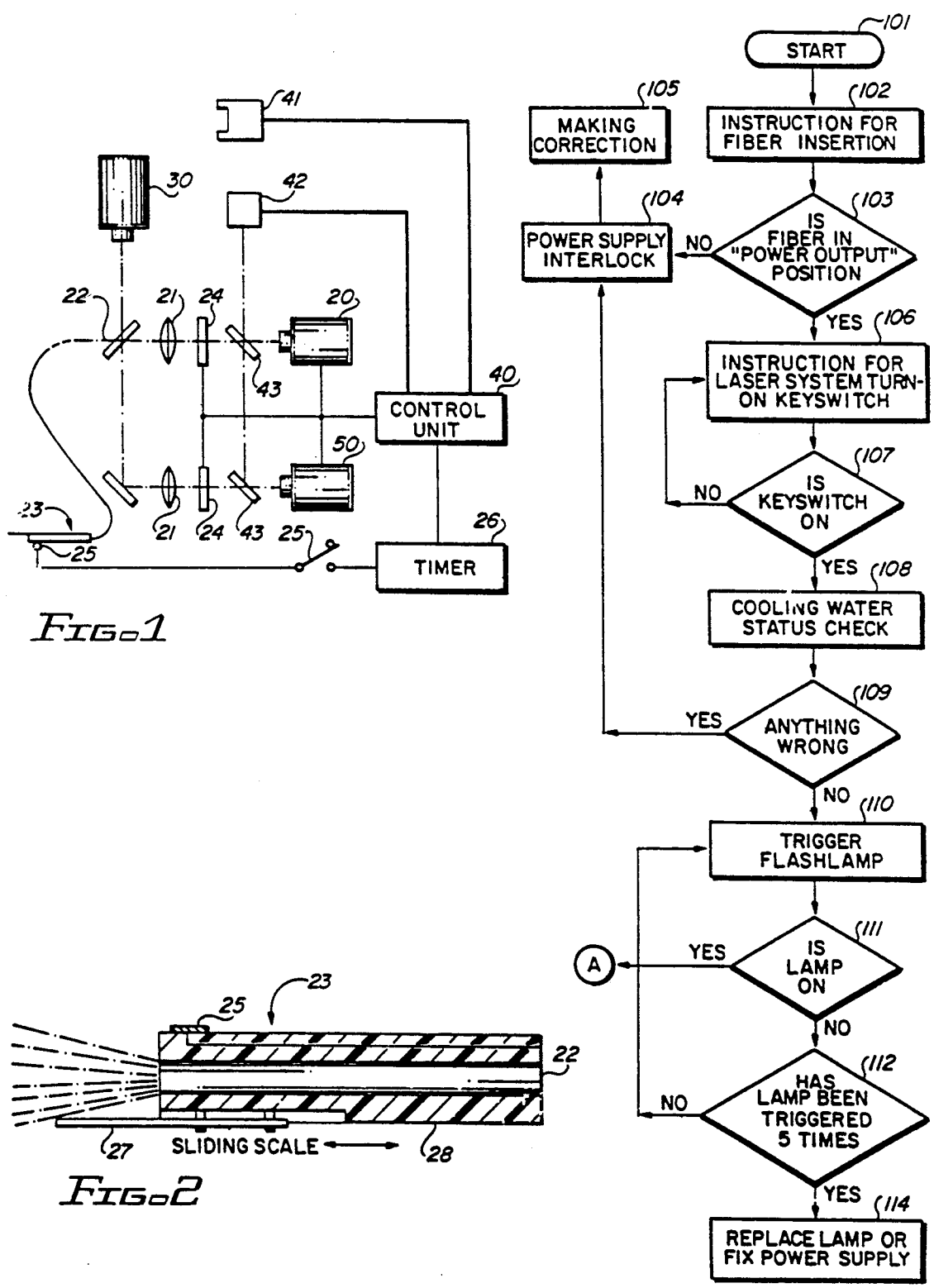

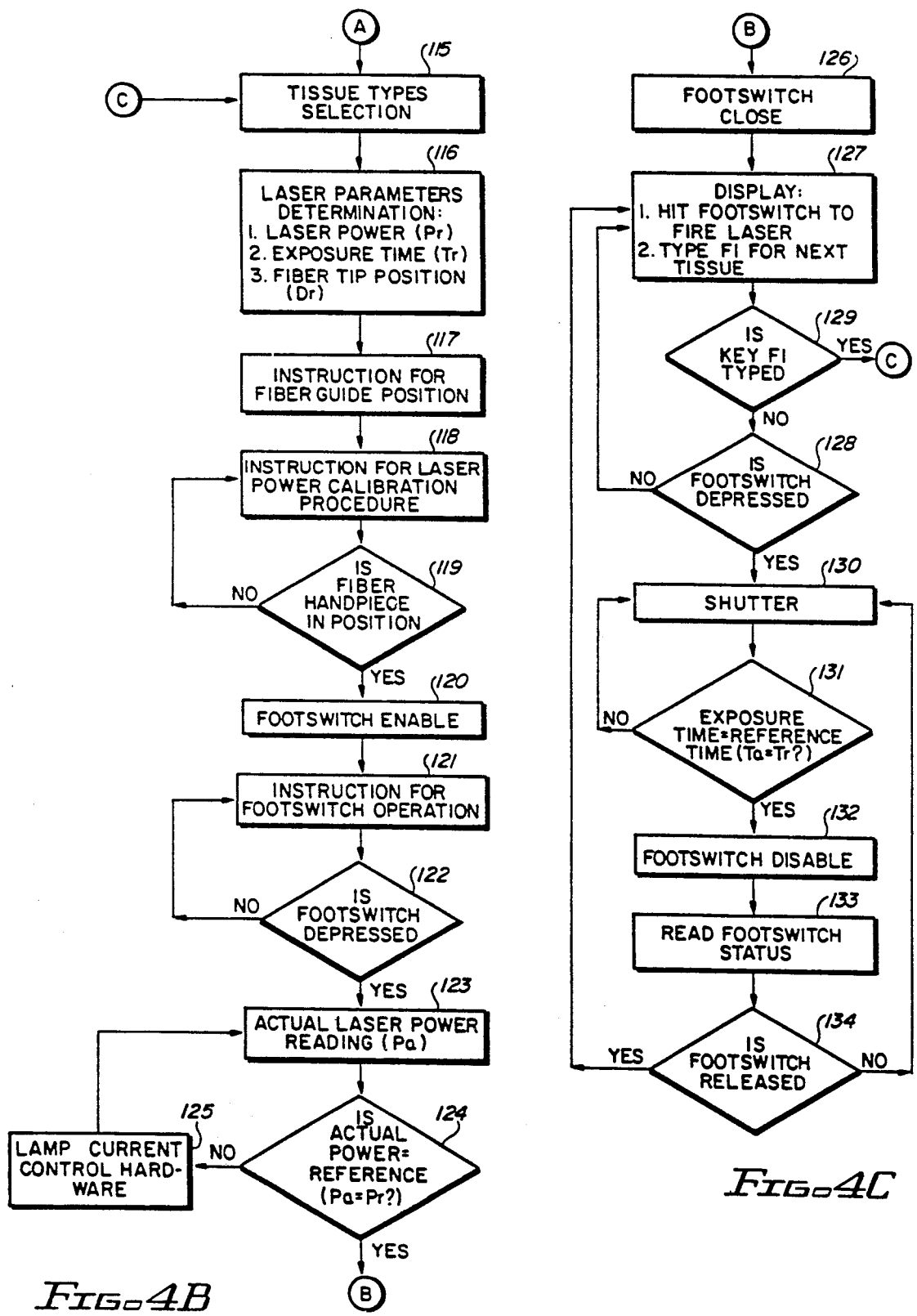

LASER HEALING METHOD AND APPARATUS

This is a continuation of co-pending application Ser. No. 07/380,622, filed Jul. 14, 1989, now U.S. Pat. No. 5,002,051, which is a divisional of Ser. No. 07/062,861, filed Jun. 16, 1987, now U.S. Pat. No. 4,854,320, which is a continuation-in-part of application Ser. No. 06/539,527, filed Oct. 6, 1983, now U.S. Pat. No. 4,672,969.

BACKGROUND OF THE INVENTION

This invention relates generally to methods and apparatus for closing wounds and more particularly, to a method and apparatus for applying optical energy to biological tissue whereby the tissue is converted to a collagenous, denatured protein substance which joins severed tissues and closes wounds.

Historically, suturing has been the accepted technique for rejoining severed tissues and closing wounds. Suturing has been achieved with a surgical needle and suturing thread, and more recently, with a variety of polymeric or metallic staples. The intended function of sutures is to hold the edges of the wounds against one another during healing so as to reduce discomfort, pain, scarring, and the time required for healing.

It is a problem with known suturing systems that since they are applied intermittently along a wound, they permit gaps in the wound between sutures to remain open thereby accepting dirt and bacteria. Moreover, in addition to producing a relatively high risk of infection and tissue rejection, such gaps between sutures are eventually filled in by keloid, which results in disfiguration and scarring. In addition, inflammation often results from the foreign body presence of the suture material.

It is an additional disadvantage of conventional sutures that they may slip in an axial direction thereby permitting relative motion between the tissues which are desired to be joined, and may loosen before the healing process has advanced sufficiently to maintain a tight closure of a wound. Thus, sutures must frequently be removed and replaced, thereby requiring multiple visits to a physician. There is a need, therefore, for a wound closure system which is uniform throughout the length of a wound.

A variety of cauterization and cryogenic techniques have been developed to reduce the flow of blood in an open wound, or a surgically-induced incision. Generally, cauterization is achieved by using intense heat to sear and seal the open ends of the tissues, such as vessels and capillaries. In known cauterization systems, heat is generated by resistance heating of a metallic probe which is subsequently applied to the tissue to be cauterized. Alternatively, undesired blood flow is discontinued by applying a cryogenic temperature which freezes the tissue. More recently, the medical field has utilized high intensity optical energy generated by one or more lasers to achieve cauterization which limits blood flow. In such known laser systems, the optical energy is applied in sufficient quantity to sear or burn the vessels. Laser cauterization is illustratively described in U.S. Pat. No. 4,122,853 to Michael R. Smith. These techniques, however, destroy the surrounding tissue leading to longer healing times, infection, and scarring.

Recent advances in the state of the art have produced cauterization with the use of ultrasonic energy which is converted to mechanical vibrations through a knife. Such a rapidly vibrating knife simultaneously cuts and closes off severed vessels. A system of the ultrasonic vibrational type is described in U.S. Pat. No. 3,794,040 which issued to Balamuth. In the known system, ultrasonic energy is applied to create heating of the vessels desired to be cauterized above room temperature, but below a temperature at which such vessel would sear. The heat thus produced causes hemostasis, by denaturing of the proteins in the tissue to form a collagenous substance which performs as a glue to achieve the closure or bond. This technique, however, has not gained widespread use for delicate surgery because it requires bringing a vibrating probe into contact with the tissue to be affected. Morever, ultrasonic energy is nonpreferentially absorbed and affects all of the surrounding tissue.

Optical energy generated by lasers has been applied in recent times to various medical and surgical purposes because the monochromatic and coherent nature of the light generated by lasers has been shown to have absorbency characteristics which vary with the nature of the illuminated tissue. Thus, for a given tissue type, the laser light may propagate through the tissue, substantially unattenuated, or may be almost entirely absorbed. Of course, the extent to which the tissue is heated, and ultimately destroyed, depends on the extent to which it absorbs the optical energy. It is generally preferred that the laser light be essentially transmissive in tissues which are desired not to be affected, and absorbed by the tissues which are to be affected. For example, when using lasers in fields which are wet with blood or water, it is desired that the optical energy not be absorbed by the water or blood, thereby permitting the laser energy to be directed specifically to the tissues desired to be affected. Such selective absorption also permits substantial time saving during an operation by obviating the need for cleaning and drying the operating field.

It is a further known advantage of a laser system that the optical energy can be delivered to the tissues desired to be operated upon in a precise location and at predeterminable energy levels. The precision with which the laser energy can be directed is enhanced by its ability to be guided by known thin optical fibers which permit the optical energy to be utilized within a body without requiring large incisions or to be inserted into the body through an endoscope. The optical fibers which conduct the laser-generated optical energy for performing the operation can be combined with other optical fibers which conduct light in the visible range, and further optical fibers which are of the image-transmissive type such that a surgeon may view and control an operation which is occurring within a body.

Ruby and argon lasers which are known to emit energy in the visible portion of the electromagnetic spectrum have been used successfully; particularly in the field of ophthalmology to reattach retinas to the underlying choroidea and to treat glaucoma by perforating anterior portions of the eye to relieve intraocular pressure. The ruby laser energy has a wavelength of 0.694 micrometers and, thus, appears red. The argon laser emits energy at 0.488 and 0.515 micrometers, thus, appearing blue-green. The ruby and argon laser beams are minimally absorbed by water, such as tissue water, but are intensely absorbed by the blood chromagen hemoglobin. Thus, the ruby and argon laser energy is poorly absorbed by nonpigmented tissue such as the cornea, lens, and vitreous humor of the eye, but is preferentially absorbed by the pigmented retina where it can then exert a thermal effect.

Another type of laser currently in surgical use is the carbon dioxide ($CO_2$) gas laser which emits a beam which is intensely absorbed by water. The wavelength of the $CO_2$ laser is 10.6 micrometers and therefore lies in the invisible, far infrared region of the electro-magnetic spectrum. Reference to FIG. 1A shows that the absorption of energy by water in this part of the spectrum is so great that it is absorbed independently of tissue color by all soft tissues having a high water content. Thus, the $CO_2$ laser makes an excellent surgical scalpel and vaporizer. Since it is so completely absorbed, its depth of penetration is shallow and can be precisely controlled with respect to the surface of the tissue being operated upon. The $CO_2$ laser is frequently used for neurological surgery where it is used to vaporize or coagulate neural tissue with minimal thermal damage to underlying tissues.

The fourth commonly used type of laser is the neodymium doped yttrium-aluminum-garnet (Nd:YAG) laser. The Nd:YAG laser ha a predominate mode of operation at a wavelength of 1.06 micrometers in the near infrared region of the electromagnetic spectrum. As discussed in copending application Ser. No. 539,527, the Nd:YAG emission at 1.06 micrometers wavelength is absorbed to a greater extent by blood than by water making it useful for coagulating large bleeding vessels. The Nd:YAG at 1.06 micrometers laser energy has, for example, been transmitted through endoscopes to treat a variety of gastrointestinal bleeding lesions, such as esophogeal varices, peptic ulcers, and arteriovenous anomolies.

It is characteristic of all of these known uses of laser energy that the tissue thus exposed is destroyed by searing, charring, or vaporization. It is therefore an object of this invention to utilize laser energy either to heal or reconstruct tissue, rather than to destroy tissue.

It is also an object of this invention to replace surgical sutures or staples in wound closures by a technique which creates an immediate seal of the severed tissue, is faster, requires minimal surgical manipulation of tissue, reduces possibility of infection, and minimizes scarring.

It is another object of this invention to use the body's own tissue elements to form a seal or a bond between severed elements of tissue.

It is still another object to use electro-optical energy to form a collagenous bonding tissue which is similar in composition to the tissue from which it is produced.

It is yet a further object of the invention to provide wound closure and reconstruction, inter alia, of the following tissues: skin, nerve fiber, vascular tissues, reproductive tissue structures such as vas deferens or fallopian tubes, gastrointestinal tract, eye tissues, and tendons.

It is also a further object of the invention to provide the wound closure and reconstruction of the above-identified tissues quickly, with little or no scarring, and with minimal risk of infection.

It is a still further object of the invention to use laser energy having a low absorbance in a bloody or wet field to increase the utility of the laser within the normal operating fields.

It is still another object of the invention to utilize a laser energy which is not preferentially absorbed by either blood or water, thereby enabling a low temperature thermal effect to be produced upon a desired tissue with deeper penetration and with substantially reduced risk of damaging neighboring tissues.

It is also another object of the invention to provide a laser apparatus which is automated and portable for effecting closure of wounds and reconstruction of tissues.

SUMMARY OF THE INVENTION

The foregoing and other objects are achieved by this invention which provides a method and apparatus for the controlled application of optical energy to convert biological tissue into a collagenous substance for facilitating healing and wound closure. In accordance with the invention, responsive to an input signal representative of a characteristic of the tissue for which closure is sought, the parameters of a generated beam of optical energy guided to the area of the intended juncture are controlled to cause the amount of optical energy delivered to the tissue in the vicinity of the wound to be within a tissue nondestructive range that causes the tissue to be converted to a denatured proteinaceous collagenous substance which forms a biological glue that closes the wound.

The intensity of the optical energy is controlled such that the rate at which such optical energy is absorbed by the tissue in the vicinity of the wound and converted into thermal energy is within a tissue nondestructive range bounded by a minimum absorption rate at which the tissue is converted to a collagenous substance and a maximum absorption rate above which the water contained in the tissue wound boil.

In accordance with the invention, a beam of optical energy is produced by a source, illustratively a laser, having a wavelength selected such that the optical energy is propagated without substantial attenuation through water and/or blood, but is absorbed in the biological tissue desired to be repaired. Such substantially unattenuated transmission through water and blood simplifies surgical procedures by obviating the need for operation in a dry, clean field. The arrangement is further provided with a guide, such as a flexible optical fiber, for directing the beam of optical energy to the wound in the tissue. Moreover, the arrangement is provided with means for controlling the parameters of the beam so that the delivered energy is controlled to remain at a level above which the tissue in the vicinity of the wound is converted to the collagenous substance, but below a level at which water in the tissue being repaired would boil.

In an embodiment of the invention, described in greater detail below, the optical energy source is constituted by a Nd:YAG laser which is tuned or is tunable to 1.32 microns. Beam intensity control is provided by circuitry that regulates the laser power source. The flexible optical fiber is provided with a shutter and timer on a foot or hand operated switch to regulate exposure time. The optical fiber is provided with a hand-piece that includes a sliding scale which sets beam spot size at the tissue by establishing the working distance between the beam emitting end of the hand-piece and the tissue being operated on. In response to input information on tissue type and thickness, a microprocessor establishes the parameters for the beam intensity control circuitry, shutter timer and hand-piece scale required to achieve the proper energy level for tissue welding.

BRIEF DESCRIPTION OF THE DRAWINGS

Embodiments of the invention have been chosen for purposes of illustration and description, with reference to the accompanying drawings, wherein:

FIG. 1 is a schematic view of a laser surgical system for use in accordance with the invention;

FIG. 2 is a side sectional view of the hand-piece of FIG. 1;

FIGS. 4A, 4B and 4C are flow diagram of a software program for use by the microprocessor of FIG. 3.

DETAILED DESCRIPTION OF PREFERRED EMBODIMENTS

Figure 3:
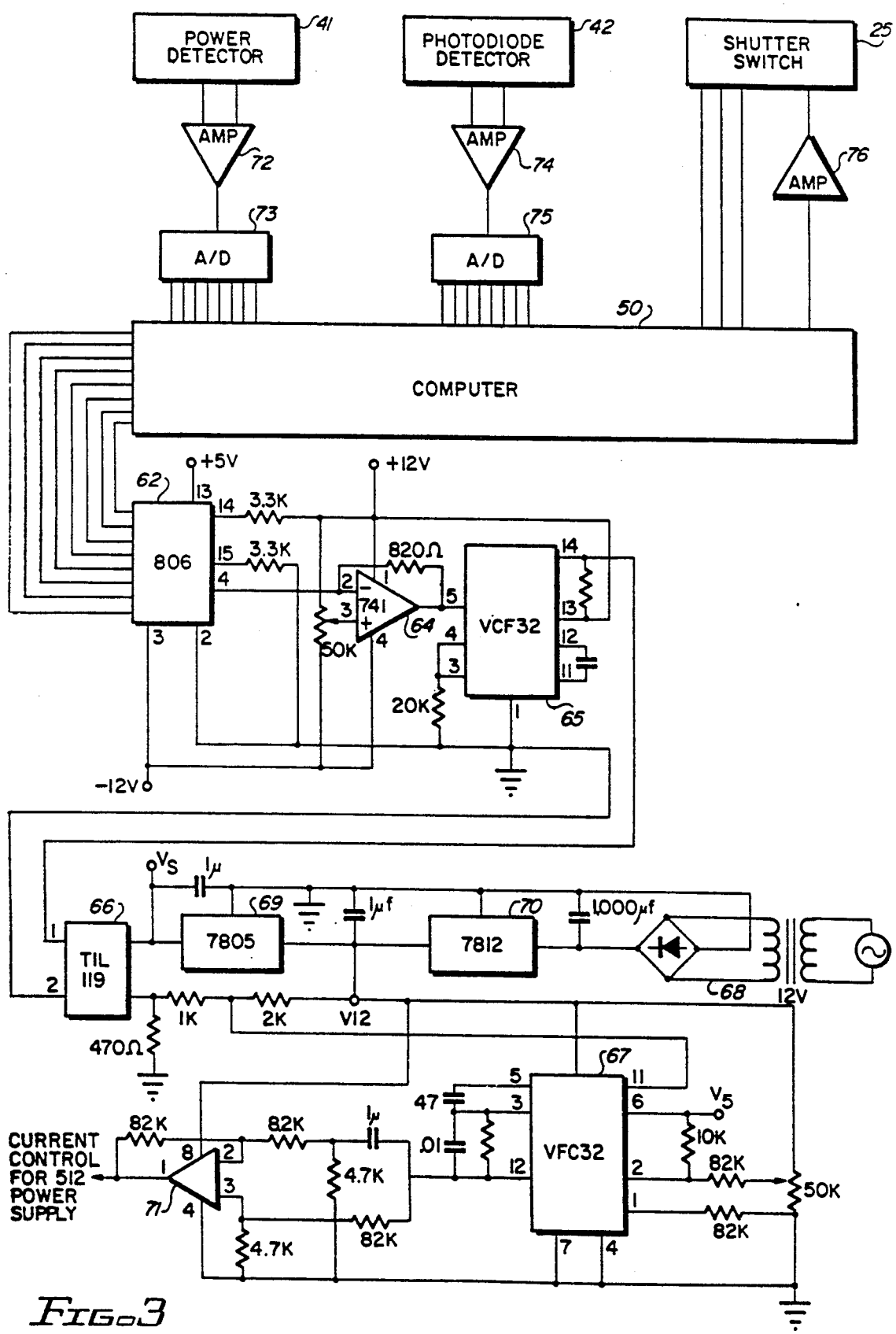
FIG. 3 is a block and schematic diagram of microprocessor control circuitry usable in the system of FIG. 1.

Biological tissue comprises cell layers in a protein framework for tensile strength. All proteins are amino acids which have side chains which are dissolvable either in water or fat. Naturation is a process wherein the amino acids fold over, always in the same configuration for each protein type, when the protein leaves the interior of a cell and is confronted with tissue water. In such case, the hydrophobic portion of a side chain folds to the interior of the molecule. The proteinaceous components of the tissue can be unfolded or denatured by the application of heat.

As stated in copending application Ser. No. 539,527, it has been discovered that application of optical energy to biological tissue, in a nondestructive amount sufficient to generate enough heat to denature the proteinaceous components, can be used to cause the body's own tissues to substantially reproduce the prior tissue structure at a wound or severed tissue site. In particular, energy from an optical energy source, such as a laser, can be applied to bring the temperature of biological tissue somewhere above room temperature, but below the point of water; preferably above 45 degrees centigrade and particularly to about 60–70 degrees centigrade. Collagen, a major source of protein in the body, is denatured by application of such energy in such a way as to go into solution and form a "biological glue" to seal a lesion, anastomize a severed vessel, or reconstruct damaged tissue. When the source of heat is removed, the proteins begin to re-nature and form an approximate replication of the prior tissue structure. As the body heals, the so-called "biological glue" will be reabsorbed and replaced by natural tissue.

The application of heat, to form a collagenous seal to immediately close a lesion or anastomize a severed vessel accelerates healing time, leaves little or no scarring, preserves the tissue, and avoids inflammation and/or infection caused by the inclusion of foreign suture material in a wound.

Optical energy of a particular wavelength is converted to heat in tissue which absorbs energy at that wavelength. As detailed in copending Ser. No. 539,527, it was discovered that optical energy having a wavelength of 1.2 to 1.4 micrometers is relatively unattenuated in both water and blood and, so, is particularly advantageous for use as an optical energy source for the formation of a "biological glue" in order to effect repair of gastrointestinal tract tissue, close skin wounds (whether originating accidentally, intentionally or through biological processes), and repair and reconstruct tissue such as reproductive tissue, tendons, and vascular tissue, provided the intensity, exposure time and spot size of the beam at its point of incidence on the tissue are controlled to keep the energy absorption by the tissue within the desirable range. A suitable wavelength is obtainable using a commercially available Nd:YAG laser configured to generate optical energy at a wavelength of about 1.32 micrometers.

FIG. 1 illustrates a surgical system for achieving tissue welding in accordance with the invention. The system has a source of optical energy, laser 20, which is preferably of the Nd:YAG crystalline variety wherein an yttrium-aluminum-garnet (YAG) rod is doped with neodymium (Nd) ions as the active light-producing element. Such a laser 20 includes a resonant cavity for amplifying the emitted light and pumping means, such as a dc Krypton arc lamp, for supplying energy to create a population inversion of the normal energy state of Nd ions. The population inversion results in the stimulated emission of light according to well-known known laser principles.

Absent any tuning of the laser cavity, Nd:YAG lasers will emit light at a fundamental dominant wavelength of 1.06 micrometers. Such lasers also emit light at a secondary wavelength of approximately 1.32 micrometers. Proper utilization of this secondary mode in laser operation requires the dominant emission, which has a greater amplitude than the secondary emission, to be suppressed. Typically, peak power output at this secondary emission level is 20–30% of the continuous wave peak power output at the dominant level. It is the secondary wavelength that is utilized in the method and apparatus of the invention.

As readily understood by persons skilled in the art, laser 20 includes a power supply circuit for activating the pumping arc lamp and cooling means for cooling the laser. A suitable Nd:YAG laser for use in this invention is produced by Control Laser Corporation, Orlando, Fla. 32809.

A lens 21 is provided to focus the emerging coherent light beam from laser 20 into an optical fiber 22. Lens 21 may comprise a system of lenses. Optical fiber 22 can be of any known type, which efficiently transmits the desired wavelength. Optical fiber 22 provides a flexible conduit for guiding the optical energy from the laser into a hand-piece or wand 23 which is manipulable by the physician. A shutter 24 is located, preferably, between laser 20 and lens 21. Hand-piece 23 contains a shutter switch 25 which controls release of the laser energy and which may be actuated by either the hand or the foot of the operator. A timer 26 is provided to control the shutter and, thereby, the duration of energy exposure. Hand-piece 23 may include a lens (not shown) for focusing or defocusing the beam.

Advantageously, hand-piece 23 includes means to enable the physician to set the working distance between the tissue to be irradiated and the distalmost end of the optical fiber or lens. In an illustrative embodiment, as shown in FIG. 2, a sliding scale 27 which cooperates with a protective case 28 on the end of optical fiber 22 controls the working distance, and hence, the diameter of the beam spot. As shown in FIG. 2, the divergence of the beam is used to control the beam diameter as the distance between the distalmost end of the fiber 22 and the tissue is increased or decreased.

For a given suitable optical wavelength and mode or beam geometry, the following electro-optical parameters require proper adjustment for each type of tissue: output power, time exposure and beam spot size. In particular, the thermal effects on the tissue can be controlled by proper selection of the electro-optical parameters. Power density measures the energy concentration of the applied light beam and is typically expressed in watts per square centimeter area of the applied beam spot. Power density is directly related to the amount of heat that will be produced at a given absorptivity. Radiant exposure, expressed in joules per square centimeter, is a measure of the power density multiplied by the exposure time. If the wavelength of the applied beam is poorly absorbed, more heat can be generated by increasing the time of tissue exposure to the applied beam. Laser output power and beam spot size selections affect the power density; overall radiant exposure is affected by power density and time exposure selections.

Suitable means for control of the power output of laser 20 is provided by a control unit 40, described further with reference to FIG. 3, below. Optical output power detector 41 is provided for initial calibration of the beam of laser 20 at start-up and a second detector 42, which always receives a portion of the beam of laser 20 by means of a beam splitter 43, is provided for continuous monitoring and feedback adjustment of the laser 20 output. The power delivered to the tissue surface should be maintained under 10 watts for purposes of tissue reconstruction by laser 20 as described herein. The object is to deliver a specific amount of energy per volume of tissue. For a given spot size, which is related to the volume of tissue exposed, there are many combinations of power output and time exposure which will deliver equivalent amounts of energy. To-wit, power delivered to the tissue typically ranges between 1 and 4 watts; although power delivered could go as high as 10 watts if the time exposure were reduced commensurately.

In the lowest order transmission mode, $TEM_{oo}$ specifically, a more concentrated beam results which can be used for cutting purposes at higher power output or for achieving very small beam spot size for tissue reconstruction. In the alternative, multimode transmission can be used for tissue reconstruction, but the beam spot size can not be as finely focused as the $TEM_{oo}$ mode. However, if the beam is defocused, less power is delivered per unit area.

As will be understood, the selection of the various electro-optical parameters for each tissue type is made as a result of skill and experience; but is determinable without undue experimentation by one of ordinary skill in the art.

In a particularly advantageous embodimient, data relating to appropriate settings of electro-optical parameters for various tissue types can be coded on a computer memory device, such as floppy disc or programmable read-only memory computer chip. The functions of control unit 40 and timer 26 can be computer controlled to adjust automatically the power level, and time exposure and display the proper spot size upon input of tissue type and the operating conditions by the physician or surgeon.

The system of FIG. 1 also includes a marker laser 30, illustratively a low-power helium-neon laser, which is coaligned with the infrared beam of laser 20. Laser 30, however, can be of any type which emits radiation in the visible range of the electromagnetic spectrum. The power rating of the helium-neon marker laser 30 is between 1-5 Watts. Marker laser 30 can be arranged so that its focal point coincides with that of the main operating laser 20 by any known technique.

As an optional feature, in order to permit the use of the laser apparatus of FIG. 1 on very thin tissue or tissue upon which only surface heating is desired, such as epineurium of nerve tissue, an auxiliary source of optical energy 50 can be incorporated into the apparatus to emit radiation having a wavelength which is intensely absorbed by biological tissue. A carbon dioxide laser, of any known type, would be a suitable auxiliary source. Source 50 is also preferably arranged so as to have its output beam coincide with the beam from marker laser 30.

It should be further pointed out that provision can be made for permitting selection of the 1.06 micrometer wavelength of the Nd:YAG laser 20 by means which are well known in the art for the purposes of tissue coagulation and wound hemostasis, as desired.

FIG. 3 shows suitable circuitry for implementation of the functions of the control unit 40 and timer 26 which utilizes a microprocessor 50, such as provided in an IBM PC/AT computer, for controlling parameters of the optical beam so as to deliver the appropriate amount of energy to the tissue reconstruction site. In response to input by the physician of the applicable tissue type and thickness, the computer 50 accesses a data base stored in a memory device to establish appropriate settings for power level, time exposure and spot size.

Optical output power is controlled by delivery of a signal from the microprocessor to the conventional current control circuitry for the power supply of the laser 20. A digital-to-analog converter 62 is connected to receive a digital current control signal from the microprocessor 50. The analog output of the converter 62 is amplified by an amplifier 64 and then converted to a frequency signal by a voltage-to-frequency converter 65. The output of the converter 65 is used via an isolating circuit 66 to drive a frequency-to-voltage converter 67 to deliver a signal from a power source 68 and voltage regulators 69, 70 through an amplifier 71 to the power control input of the laser 20 (e.g. the current control circuitry for a Control Laser Model 512 power supply). The isolation between the computer 50 and the laser 20 is provided for protective purposes and may be achieved through use of an optocoupler.

Verification of power setting accuracy is accomplished initially by requiring that the wand 23 end of the optical fiber 22 be inserted in the calibration port of power detector 41 located in a system console (not shown).

The power detector 41 may take the form of a coherent power detector, such as a thermal calorimeter. Following determination by the computer 50 of the correct power setting for the laser 20 for a particular tissue type and thickness, at first fire-up of the lamp the hand-piece or wand 23 is inserted in a receptacle on the control unit console. Initial firing of the laser is prevented unless the hand-piece 23 is in the receptacle. The output of the detector 41 is amplified by an amplifier 72 and converted in an analog-to-digital converter 73 for input to the microprocessor 50. The microprocessor 50 then performs a calibration subroutine to adjust the digital output to the converter 62 and thus to the laser power source, until the desired optical power output is read at the power detector 41. If the intensity of the beam output is too low, the value of the digital signal to converter 62 is incremented; if the output is too high, it is decremented. The microprocessor 50 will then clear the system for operation outside of the receptacle under control of the shutter switches 25 and timer 26.

Subsequent beam output adjustment is undertaken by microprocessor 50, in accordance with well-known principles, by which a small amount of the optical output is diverted by the beam splitter 43 (FIG. 1) for measurement by the detector 42, which suitably takes the form of a photodiode connected through an amplifier 74 and an analog-to-digital converter 75 to deliver a power level input to the microprocessor 50. The photodiode 42 circuit provides a continuous feedback loop through the microprocessor 50 for power output vertification.

As already indicated, a shutter switch 25 (FIG. 1) is provided control to emission of the beam toward the tissue. For control of the total energy applied, the computer 50 also serves the function of a timer 26 (FIG. 1) to limit the total time for which shutter 24 permits the beam from laser 20 to reach the tissue on any one shot. The shutter 24 is arranged to normally be in a beam blocking position. The switch 25 is connected to the computer 50 with the aid of an amplifier 76, as shown in FIG. 3, and programming is provided so that a counter is set up to increment for each clock pulse received during the time that shutter 24 is open. When the count indicates that the total specified exposure time set by computer 52 is reached the shutter will be closed and blocked from reopening until a certain counter reset time delay has passed. This ensures that each passage of beam energy from the laser 20 will have the required energy. It will be appreciated that other arrangements for the timer 26 shutter control circuitry are possible and that, in particular, the function by programming in microprocessor 50 can be replaced by hardwired timer circuitry, if desired.

For the illustrated embodiment, the diameter of the beam spot at the point of impact with the tissue is controlled by setting the working distance from the distalmost end of the fiber 22 to the tissue. As shown in FIG. 2, this is accomplished by manual manipulation of the sliding scale 27 to achieve the distance specified by the computer 50 to give the required beam diameter and beam energy density required for the subject tissue type and thickness. In response to input of the tissue characteristics, the computer displays the required setting. It will be appreciated that beam shaping may be accomplished in other ways and that the scale movement can be accomplished automatically, if desired. The shown means is, however, a simple workable approach that lends itself readily and inexpensively for use on a disposable optical fiber 22 for use in a sterile environment.

For input of tissue characteristics to the microprocessor 50 a conventional data input device, such as a keyboard is used. Known touch screen or voice activated input devices may also be used. It is preferable for the input process to be undertaken under prompting by tissue type and thickness selection menus appearing on a visual display.

FIGS. 4A–4C present an overall flow diagram of the software steps performed by the computer 50 for controlling the parameters of the beam in accordance with selected tissue characteristics. As a first step in readying the system for use, the computer 52 undergoes a series of checks. At the start 101 of the program, instructions are given at 102 on a display device, such as a cathode ray tube screen, for insertion of nonwand end of the fiber into the laser console. In order to engage the laser power supply, the fiber has to be in the inserted "power output" ready position. If the fiber is not in the correct position the power supply to the system will be disabled at 103, 104, preventing operation of the laser 20 until a correction is made at 105. The illustrated embodiment contemplates the use of a key switch on the operating console, so the program awaits the positioning of that switch into the lamp on position before proceeding. Upon receipt at 107 of the awaited keyswitch signal, the program then proceeds to do some preliminary checks, such as checking the status of the laser cooling system at 108. For example, the deionized water is checked for proper conductivity, pressure and temperature. Other checks and diagnostics can also be run. Also, security subroutines can be implemented at this or another stage to ensure that only authorized individuals operate the beam itself. Should the diagnostics or other checks indicate some discrepancy at 109, the program will be directed to block further operation of the system, as at 104. If everthing checks out, at 110, the program initiates a signal to fire the krypton lamp to activate the laser 20. A determination is made, such as by looking at the signal from detector 42 (FIG. 3), at 111 to ensure that the lamp is on. If the lamp is not on, retriggering is initiated at 112. If after five attempts, the lamp does not light, a message is displayed at 114 to replace the lamp or repair the power supply.

The program then moves to an input requesting posture to define the beam according to the tissue to which it will be applied. At 115, tissue characteristics are entered into the computer 52. A suitable way to accomplish that is to utilize a menu-driven tissue selection process. Available tissue selections are displayed on the screen, and input is solicited. Once tissue type is entered, the menu will be changed to solicit input as to tissue thickness. When tissue thickness has been selected, the computer 52 addresses data stored in a memory device, such as a disk in a disk drive, and at 116 determines the laser operation parameters appropriate for the selected tissue characteristics.

It is advisable to provide some feedback to the user on tissue type and thickness to guard against input error. This can be done using any of several well known techniques. One way is to display graphic representations of the selected tissue type and thickness on a display screen to provide an easily identifiable visual check to give reassurance to the user.

For the embodiment described, the laser parameters obtained from lookup in the memory storage device include a combination of laser power (Pr), exposure time (Tr) and fiber tip position (Dr) settings that will deliver a controlled amount of optical energy to the selected tissue type and thickness to nondestructively convert it to a denatured proteinaceous collagenous substance to close join it together.

The laser power and exposure time parameters are fed to assembly programs for direct control of the power and shutter control circuitry described perviously. For manual adjustment of the beam spot diameter in the manner contemplated by the described embodiment, instructions for manual setting of the fiber guide sliding scale 27 to establish the correct fiber tip position (Dr) are displayed on the screen at 117.

Once the parameters are determined and the distance guide 27 set, instructions are displayed at 118 for initial calibration of the beam. At 119, the program checks to ensure that the fiber hand-piece 23 is properly inserted into the receptacle part of the power detector 41 (FIG. 3). For safety reasons, if the fiber hand-piece is not in the sensor position at this stage, the program loops back to 118. Switch 25 is enabled at 120 to permit operation of the shutter 24 for initial calibration. Instructions for footswitch (handswitch) operation are given at 121.

Shutter switch 25 actuation is monitored at 122. At 123-125, the actual laser beam output reading (Pa) detected by the detector 41 (FIG. 3) is compared with the computer 50 designated reference output Pr. The lamp current control hardware is adjusted until the measured output power is the same as the computer specified output power. The switch 25 is then closed at 126. The shutter 24 will shut as soon as Pa=Pr is established. Initial calibration over, the laser is now set for tissue use.

Through menu selection choice or other input procedure as shown at 127, the user can now proceed to control the shutter 24 with the switch 25 at 128 in order to conduct the tissue joining process. Alternatively, the user can elect at 129 to revise the parameters to those more suited to another tissue, whereupon the program will repeat the previous steps.

Depressing the switch 25 will open the shutter 24 for tissue welding at 130. The shutter open time will be monitored as already described, with the shutter 24 closing when the timed actual exposure time Ta reaches the specified exposure time Tr, at 131. When the computer set exposure time Tr is reached, the footswitch is disabled at 132 and footstitch status (depressed or released) is determined at 133. When the footswitch is released, the timer is reset and the program directed back to step 127 to ready the system for another shot.

The program can be modified and embellished to meet specific needs. It can be integrated with a program to display patient case history data and to update the patient file automatically to record the details of the procedure applied to that patient.

In an illustrative embodiment, the apparatus of FIG. 1 is used for skin closure at a lesion site. The tissue edges of the lesion are brought into close approximation by manual manipulation, for example. Hand-piece 23 is positioned above the lesion at such a distance as to produce the desired beam spot size. The power, time exposure and spot size are set so as to heat the tissue above 45 degrees centigrade, but below the boiling point of water (100 degrees centigrade). Typical spot sizes range from 0.1 mm to 1.0 mm for levels of power delivered to the tissue ranging from 1 to 5 watts, and time durations ranging from 0.05 to 5.0 seconds. When the optical energy of laser 20 at 1.32 micrometers is released on the lesion site, with the electro-optical parameters adjusted as hereinabove suggested, the tissue at the lesion site is heated to a temperature sufficient to cause denaturization of the tissue proteins to the depth necessary to reconstruct the tissue in the lesion irrespective of whether the operating field is bloody or wet. The electro-optical parameters are set and controlled in response to input as to tissue type and thickness. Parameters may be specified for the reconstruction of many soft tissues such as vascular structures, tendon, vas deferens, fallopian tubes, gastrointestinal tract, dura, and sclera. With an appropriately controlled modification of the level of power delivered to the tissue under repair, cartilage and tympanic membranes can also be repaired in accordance with the invention described hereinabove.

The above-described embodiments are provided for the purpose of illustration and are not to be construed as limiting. Other modifications and adaptations can be made by those of skill in the art without departing from the spirit and scope of the invention. In particular, the laser energy can be transmitted to the patient treatment site by an articulated arm with mirrors or it can be transmitted to the interior of a patient by endoscope. Moreover, materials other than neodymium-doped crystalline yttrium-aluminum-garnet can be used as a lasing medium to generate optical energy at the desired wavelengths.

What is claimed is:

1. Apparatus for automatically controlling the application of energy in the reconstruction of biological tissue to cause the formation of a proteinaceous framework from denatured protein in the vicinity of the biological tissue, the framework approximating the biological tissue to be reconstructed, the apparatus comprising:

an energy source for producing energy which is capable of heating the tissue to form an adhesive proteinaceous substance;

guide means for directing the energy to heat a spot on a biological tissue to be reconstructed, the guide means having a distal most end remote from the energy source and from which the energy is emitted;

data conversion means responsive to a user input signal containing characteristics of the tissue for generating an output signal representative of control parameters for the energy source to cause substantially all of the tissue heated to be within a non-destructive range bounded by a minimum rate at which the proteinaceous components of the tissue denatures and a maximum rate at which the water in the tissue would boil; and means operatively connected to the source and to the data conversion means for controlling the energy source in accordance with the control parameters.

2. A method for the controlled application of radiative energy in the reconstruction of biological tissue to cause the formation of a proteinaceous framework from denatured protein in the vicinity of the biological tissue, the framework approximating the biological tissue to be reconstructed, the method comprising the steps of:

generating an input signal representative of a characteristic of tissue to be reconstructed;

analyzing the signal to determine suitable parameters, based on stored information, of a radiative energy beam to be delivered to the tissue site at a desired energy level within a tissue non-destructive range bounded by a minimum rate at which tissue denatures and a maximum rate at which water in the tissue would boil, whereby proteinaceous components of the tissue are denatured; and using the parameters to control the power, the exposure and diameter of the radiative energy beam to the tissue, such that substantially all of the energy delivered by the beam to the tissue is maintained at the desired energy level.

* * * * *